United States Patent [19]

Ito

[11] 4,051,025
[45] Sept. 27, 1977

[54] PREPARATIVE COUNTERCURRENT CHROMATOGRAPHY WITH A SLOWLY ROTATING HELICAL TUBE ARRAY

[75] Inventor: Yoichiro Ito, Bethesda, Md.

[73] Assignee: The United States of America as represented by the Department of Health, Education and Welfare, Washington, D.C.

[21] Appl. No.: 727,864

[22] Filed: Sept. 29, 1976

[51] Int. Cl.[2] .............................................. B01D 15/08
[52] U.S. Cl. ................................ 210/31 C; 210/198 C
[58] Field of Search ................. 210/31 C, 198 C, 267; 55/67, 197, 386, 78, 390

[56] References Cited

U.S. PATENT DOCUMENTS

| | | | |
|---|---|---|---|
| 3,038,326 | 6/1962 | DeFord | 55/386 |
| 3,617,557 | 11/1971 | Giltrow | 210/31 C |
| 3,775,309 | 11/1973 | Ito et al. | 210/198 C |
| 3,856,669 | 12/1974 | Ito et al. | 210/198 C |

Primary Examiner—John Adee
Attorney, Agent, or Firm—Browdy and Neimark

[57] ABSTRACT

A method and apparatus for continuous countercurrent chromatography employing a coiled column array slowly rotating about its axis, mounted on a frame which can be angularly adjusted to a desirable angle. The column can be filled with a stationary phase liquid and eluted with a mobile phase liquid by means of a pump; solute can be introduced through a sample port. The mobile phase liquid and sample are introduced through a first rotating seal. An outlet line leading to a monitor and fraction collector is connected to the column array through a second rotating seal. When the column array is filled with the stationary phase and is eluted with the mobile phase in the proper direction, nearly half of the stationary phase may be retained while constantly mixed with the mobile phase; consequently, solutes introduced through the sample port are subjected to an efficient partition process and are separated according to their relative partition coefficients.

12 Claims, 4 Drawing Figures

PREPARATIVE COUNTERCURRENT CHROMATOGRAPHY WITH A SLOWLY ROTATING HELICAL TUBE ARRAY

FIELD OF THE INVENTION

This invention relates to the separation of samples, and more particularly to an elution method and apparatus for continuous countercurrent chromatography of the type employing a coiled tubular array rotating on its longitudinal axis.

BACKGROUND OF THE INVENTION

Centrifugal countercurrent chromatography has been successful in high efficiency analytical separation with a variety of two-phase solvent systems. For example, see Y. Ito and R. L. Bowman, (1975) Anal. Biochem., 65,310, Y. Ito and R. L. Bowman, U.S. Pat. No. 3,856,669, Dec. 24, 1975, and Y. Ito and R. L. Bowman, U.S. Pat. No. 3,775,309, Nov. 27, 1973. In these systems, two immiscible or partially soluble liquid phases are brought into contact for the transfer of one or more components. In helix countercurrent chromatography a horizontal helical tube is filled with one phase of a two-phase liquid and the other phase is introduced at one end of the helix and passes through to the first phase. In these systems, to enable the countercurrent process to take place inside a very small diameter tube having a maximum number of turns, it is desirable to enhance the gravitational field by the use of centrifugation.

However, preparative separation with low interfacial tension phase systems often becomes difficult because of emulsification of the solvent in a large bore column, resulting in carry-over of the stationary phase. See Y. Ito and R. L. Bowman, (1973) J. Chromatogr. Sci., 11, 284. Although droplet countercurrent chromatography developed for preparative purposes can be used, the efficiency of separation achieved on the low interfacial tension n-BuOH (normal butanol) phase system is no more than that of the countercurrent distribution method. See H. Yoshida, C. L. Zimmerman and J. J. Pisano, (1975) Proceedings of the Fourth American Peptide Symposium, 955.

SUMMARY OF THE INVENTION

Accordingly, a main object of the present invention is to overcome deficiencies in the prior art, such as indicated above. Another object is to provide for improved countercurrent chromatography.

Yet another object is to provide a simple preparative countercurrent chromatographic system which substantially improved the results obtained by the above-mentioned previous systems, without relying on centrifugation.

A further object of the invention is to provide an improved preparative countercurrent chromatographic technique utilizing a helical tube array slowly rotating about its axis in a gravitational field, the technique involving the use of relatively simple apparatus and being effective to distribute the phases of a two-phase solvent system in such a way that each turn of a helical tube containing the phases finally contains about equal amounts of the two phases, and so that a dynamic equilibrium may be reached, after which further rotation results in mixing of the phases in each turn of the tube without changing the distribution pattern.

A still further object of the invention is to provide a novel and improved method and apparatus for countercurrent chromatography employing the gravitational effects produced by the slow rotation around its axis of a helical tube array containing the upper and lower phases of an equilibrated two-phase solvent system, with the provision of means to make angular adjustments of the array to provide the optimum phase retention conditions.

In furtherance of these and other objects, the following discussion generally explains a system according to the present invention:

The system uses a helical tube array slowly rotating about its own axis in a gravitational field. If the helical tube array axis is somewhat deviated from the vertical position, a particle introduced into the helical tube array moves toward one end of the tube. This end is called the "head" and the other end the "tail". When the end-stoppered helical tube array contains upper and lower phases of an equilibrated two-phase solvent system, the slow rotation of the helical tube array finally distributes the phases in such a way that each turn of the tube contains about an equal amount of the two phases and any excess of either phase occupies the tail end of the tube. Once this dynamic equilibrium is reached, further rotation results in mixing of the phases in each turn of the tube without changing the distribution pattern. This phenomenon indicates that the system possesses and ideal feature for countercurrent chromatography, i.e., phase retention and mixing.

Consequently, in the present invention, continuous countercurrent flow is produced by pumping the mobile phase through the head end of the rotating helical tube array filled with the stationary phase. The mobile phase then replaces the stationary phase, with about half of its volume in each turn of the tube and is finally eluted through the tail end of the tube. Thus, solutes introduced through the head end of the tube are subjected to a continuous partition process between the mobile and the stationary phases and are separated according to their relative partition coefficients.

BRIEF DESCRIPTION OF THE DRAWINGS

Further objects and advantages of the invention will become apparent from the following detailed description of embodiments, and from the accompanying drawings thereof, wherein.

DESCRIPTION OF A PREFERRED EMBODIMENT

Figure 1:
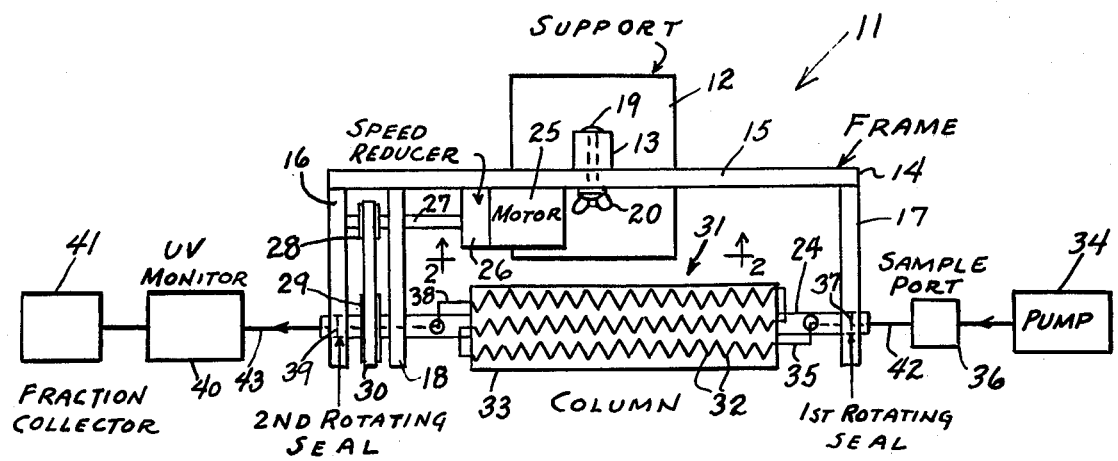
FIG. 1 is a partly schematic top plan view of an improved countercurrent chromatography apparatus according to the present invention.
Figure 2:
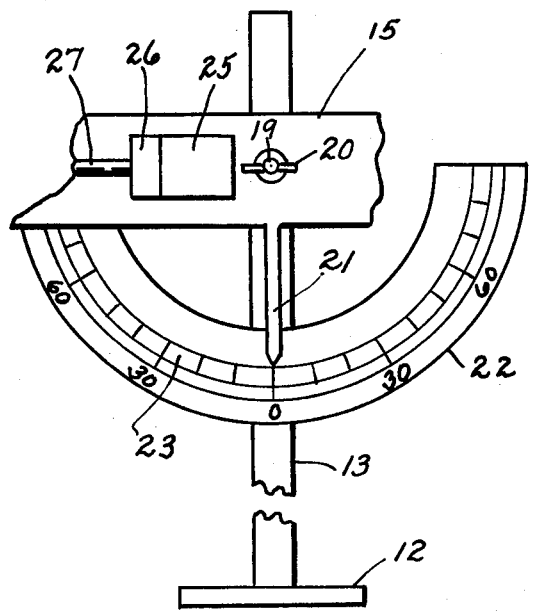
FIG. 2 is a fragmentary elevational view taken substantially on the line 2—2 of FIG. 1.

Referring to the drawings, and more particularly to FIGS. 1 and 2, 11 generally designates a typical apparatus employed in performing the technique of the present invention. The apparatus 11 comprises a supporting base 12 which may be rigidly secured on a horizontal surface and which is provided with an upstanding vertical post member 13. Designated generally at 14 is a frame comprising an elongated rear bar member 15 having forwardly projecting end arms 16 and 17 rigidly secured thereto and having a forwardly projecting inner arm 18 spaced from and parallel to end arm 16. Bar member 15 is adjustably pivotally secured at its midportion to the upper portion of post member 13 by a pivot bolt 19 provided with a clamping wing nut 20.

The midportion of bar member 15 is provided with a depending pointer 21 radially aligned with bolt 19 and extending over an arcuate angle scale plate 22 suitably rigidly secured on post member 13 below bolt 19, said plate 22 being provided with an angle scale 23 concentric with bolt 19, as shown in FIG. 2.

A hollow shaft 24 is rotatably mounted in the arms 16, 18 and 17, parallel to bar member 15. An adjustable-speed drive motor 25 provided with a suitable speed reducer 26 is mounted on bar member 15 with its output shaft 27 journalled in arms 16, 18. Respective toothed pulleys 28 and 29 are mounted on shafts 27 and 24 and are drivingly coupled by a toothed belt 30.

A helical tube column array 31 is tightly mounted around the hollow shaft 24. Said array may comprise a plurality of seriallyconnected helically coiled tube sections 32 rigidly secured on a suitable elongated cylindrical support 33 coaxially mounted on hollow shaft 24.

Each column unit 32 may be prepared by winding Teflon tubing of 2.6 mm i.d. and about 5 m. in length onto a plastic pipe of 1.25 cm o.d. and 50 cm in length, to make about 100 turns. The capacity is about 25 ml. A long column is obtained by connecting a desirable number of the column units 32 in series by tail-to-head connections. The whole column can also be made from one piece of tubing to eliminate connections. The column units 32 are tightly mounted in any suitable manner on the support 33 parallel to and extending around the rotary hollow shaft 24.

The solvent is introduced into the helical tube array 31 by a suitable pump 34 into the head end conduit 35 of the column, which extends through the right end of shaft 24, as viewed in FIG. 1, through a sample port 36 and a first rotating seal 37, while the eluate leaves the tail end conduit 38, which extends through the left end of shaft 24, through a second rotating seal 39, and is continuously monitored by an LKB Uvicord III at 280 nm, shown at 40, and then is fractionated by a fraction collector 41. Each rotating seal may be made from a pair of Kel-F blocks and a Teflon O-ring to minimize corrosion by the solvents used.

The inlet and outlet conduits, shown at 42 and 43, are of the flexible type, with sufficient slack to permit wide pivotal adjustment of frame 14. Said frame can therefore be positioned at a desired angle be rotating same and clamping it in adjusted position by means of wing nut 20, the angular position being indicated on scale 23 by pointer 21.

As previously mentioned, in operation the apparatus relies essentially on gravitational separation effects rather than centrifugation, since the rate of rotation of the helical tube column array 31 is relatively low. The separation action takes place mainly due to the gravitational forces imposed on the contents of the coils of the slowly rotating column as they change their orientations in their movement around the rotational axis of the column.

As a typical example of a mode of performing the technique of the present invention, a two-phase system composed of n-BuOH (normal butanol), $CH_3COOH$ and $H_2O$ at 4 : 1 : 5 volume ratio was selected, because of its very low interfacial tension phase property and practical usefulness. The phase mixture was gently degassed by vacuum, equilibrated at room temperature and separated before use.

Phase retention studies were made, as follows: using a single column unit, retention of the stationary phase was measured under various conditions with respect to column angle, rotational speed, and flow rate, and both upper and lower phases were tested as a stationary phase. In order to study the phase distribution and flow pattern, it was convenient to color the stationary phase with a dye which partitions almost entirely to the stationary phase. Acid fuchsin was used to color the lower phase and basic fuchsin for the upper phase. The column was first filled with the mobile phase and about 5 ml of the lightly colored stationary phase was introduced into the column, which was held vertical so that the stationary phase was completely separated from the mobile phase. The length of the column occupied by the colored stationary phase was then measured as A cm. Then the column was set to a desired test angle, rotated and eluted with the mobile phase at desired test rates. After a dynamic equalibrium was reached, the length of the column containing the colored stationary phase was measured as B cm. The retention percentage of the stationary phase, R, was then calculated as $R = A/B \times 100$.

Figure 3:
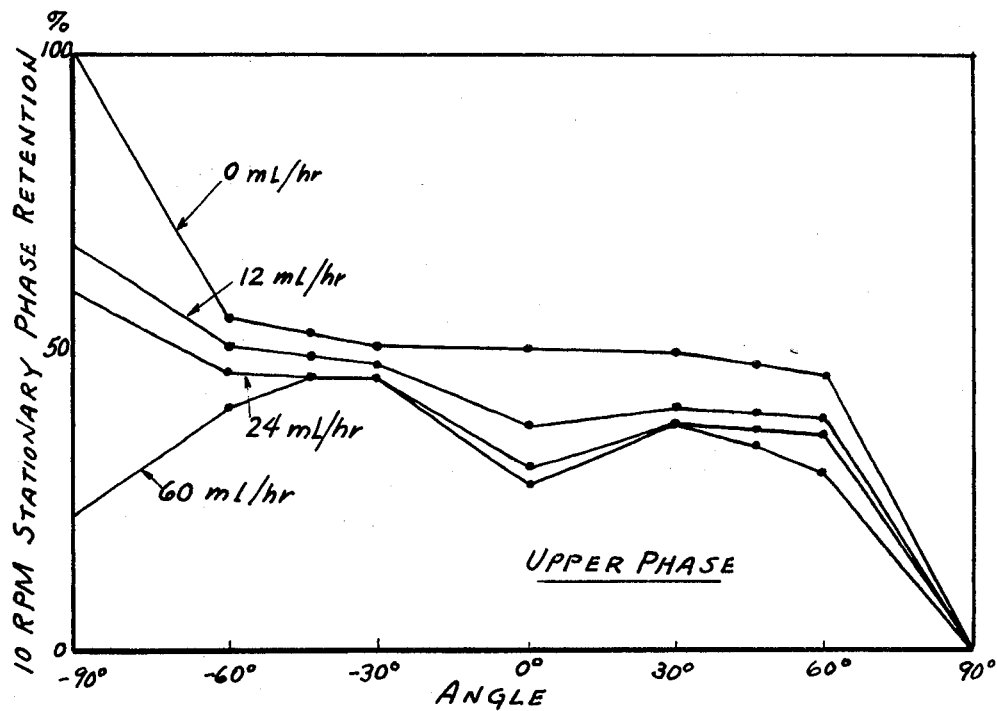
FIG. 3 is a graph showing typical retention characteristics of the upper phase component in a system according to the present invention, as a function of the angle of inclination of the rotating helical tube array and at different flow rates.

These phase retention studies were made for the upper phase as the stationary phase for rotational speeds from zero RPM to 20 RPM and for column angles from $-90°$ to $+90°$, with flow rates from 12 ml/hr to 60 ml/hr. For the lower phase as the stationary phase, the studies were made for rotational speeds from zero RPM to 10 RPM and for column angles from $-90°$ to $+90°$, with flow rates from zero ml/hr to 24 ml/hr. FIG. 3 shows a typical set of test results, for the upper phase as the stationary phase at a rotational speed of 10 RPM, wherein the retention percentage is plotted against the column angle, where 0° indicates horizontal position, $+90°$ and $-90°$ being the vertical position with the head end upward and downward, respectively. The graphs of FIG. 3 show the effect of the different flow rates. The overall results indicate that the retention of the upper phase increases with the rotational speed, and over 60 ml/hr flow rate is applicable in a wide range of angles, while the retention of the lower phase decreases somewhat with the rotational speed, and the maximum flow rate is limited to 24 ml/hr.

Most of the curves show an abrupt decrease of retention at 0°, suggesting a change of two-phase flow pattern at this angle. It was observed that at the angles over $+30°$ or below $-30°$ each phase undergoes a laminary flow along the side wall of the tube favored by the gravity condition. When the angle becomes close to 0°, the pattern changes into a segmental flow where the lower aqueous phase, having less affinity to the wall, is broken into short segments or droplets each extending across the diameter of the tube. Careful observation reveals that individual droplets move back and forth with rotation, mostly without coalescence, suggesting a high partition efficiency under this condition.

Figure 4:
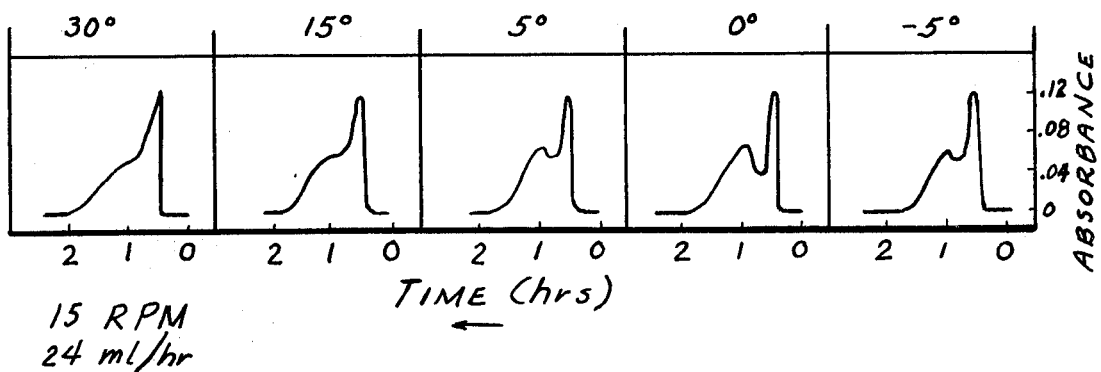
FIG. 4 is a set of graphs showing the separation of peptides in a system according to the present invention, for different angles of inclination of the rotating helical tube array, as functions of time of operation, for a given rotational speed and for a given flow rate.

Partition efficiency studies were made as follows: two pairs of peptides were selected on the basis of their partition coefficients: L-tyrosylglycyl-glycine (0.21) and L-leucyl-L-tyrosine (1.0) for studies on upper phase as the stationary phase, and L-tryptophyl-L-tryptophan (5.2) and L-leucyl-L-tyrosine (1.0) on lower phase as the stationary phase. Each sample mixture was dissolved into the lower phase and 0.2 ml of sample solution was injected through the sample port, followed by elution with the mobile phase under a given set of conditions of column angle, rotational speed and flow rate. The eluate was monitored at 280 nm. FIG. 4 shows a typical set of absorbance vs. time curves obtained, namely, at 15 RPM rotational speed for column angles from +30° to −5°, with a flow rate of 24 ml/hr. The partition efficiency may be judged by comparing the relative height of the trough between two peaks. The best separation was obtained, as shown in FIG. 4, at 15 RPM in the horizontal column position, where slight shifts (±5°) of the angle decrease the efficiency. Separation was relatively poor from zero RPM up to 10 RPM.

In the horizontal position, using various flow rates and rotational speeds, it was found that at a slow rate of 6 ml/hr at 20 RPM the highest resolution was obtained in the case where the lower phase was used as the mobile phase. Where the upper phase was used as the mobile phase, the highest resolution was achieved at a 6 ml/hr flow rate at 10 RPM rotational speed.

In general, the minumum rotational speed will be 1 or 2 RPM and the maximum will be that providing a centrifugal force not exceeding gravity, e.g. normally 150–200 RPM.

The studies showed that a separation of peptides could be achieved at an efficiency of several times that obtained by the prior-known countercurrent distribution apparatus or by droplet countercurrent chromatography. The technique of the present invention allows the use of one column for a variety of low interfacial tension two-phase solvent systems, with either phase being used as the stationary phase. The apparatus involved is relatively simple and inexpensive, so that it can be easily fabricated in a small machine shop. The technique can be used in the preparative separation of a wide range of biological materials.

While certain specific embodiments of a method and apparatus for continuous countercurrent chromatography have been disclosed in the foegoing description, it will be understood that various modifications within the scope of the invention may occur to those skilled in the art. Therefore it is intended that such modifications and adaptations are within the meaning and range of equivalents of the disclosed embodiments and may be made without departing from the invention. For example, the device may be fabricated without rotating seals; and different materials than those mentioned above can be used in fabrication and in usage, e.g. a solvent system of chloroform, acetic acid and 0.1N HCl in a volume ratio of 2:2:1 can be used for the separation of DNP – amino acid.

What is claimed is:

1. An apparatus for continuous countercurrent chromatography comprising a support, frame means pivoted to said support for rotary adjustment around a transverse horizontal axis, a separation column comprising a helical tube array and journalled on said frame means for rotation around an axis perpendicular to said horizontal pivotal axis, drive means on said frame means drivingly connected to said separation column for rotating the column, feed conduit means for introducing fluids to one end of said separation column, fluid monitoring means, and delivery conduit means connecting the other end of said separation column to said fluid monitoring means.

2. The apparatus of claim 1, and wherein the feed conduit means is provided with a sample port, and fluid pump means connected to said feed conduit means through said sample port.

3. The apparatus of claim 1, and fraction collector means connected to the outlet of said fluid monitoring means.

4. The apparatus of claim 1, and wherein said frame means comprises an elongated bar member provided with spaced forwardly projecting arms, and wherein said separation column is provided with a supporting shaft journalled in said arms.

5. The apparatus of claim 4, and wherein said drive means comprises a motor mounted on said frame means, said motor having speed reducing means drivingly coupling the motor to said supporting shaft.

6. The apparatus of claim 5, and wherein said supporting shaft is hollow, and wherein said feed conduit means and delivery conduit means extend through the opposite ends of the shaft.

7. The apparatus of claim 6, and wherein said feed conduit means and delivery conduit means include respective rotating seals.

8. The apparatus of claim 7, and wherein said elongated bar member is pivoted to said support substantially at its midportion.

9. The apparatus of claim 8, and wherein said support is provided with an upstanding post member, said elongated bar member being pivotally connected to said post member by means of a transverse pivot bolt, said pivot bolt being provided with a clamping nut for locking the bar member in a selected angular position relative to said post member.

10. A method of countercurrent chromatography comprising the steps of filling a rotary separation column comprising a helical tube array through a feed conduit with a first solvent, said separation column having a longitudinal axis of rotation, the feed conduit being located along said axis, rotating the column at a slow rate, introducing a sample solute to be separated into said column through said feed conduit, pumping a second solvent immiscible with said first solvent into the slowly rotating separation column, and spectrographically monitoring the separating solute fractions leaving the separation column.

11. The method of claim 10, and adjusting the separation column so that its axis is at an angle to the horizontal.

12. The method of claim 10, and wherein the rate of rotation of the separation column is in the range from 1 to 200 RPM.

* * * * *